United States Patent
McMillin et al.

(10) Patent No.: US 12,290,174 B2
(45) Date of Patent: May 6, 2025

(54) ILLUMINATED SHELF

(71) Applicants: SSW Advanced Technologies, LLC, Fort Smith, AR (US); Eypex Corporation, Auburn Hills, MI (US)

(72) Inventors: Matthew McMillin, Palmyra, IN (US); Matt Goodison, Auburn Hills, MI (US)

(73) Assignees: SSW Advanced Technologies, LLC, Louisville, KY (US); Eypex Corporation, Auburn Hills, MI (US)

( * ) Notice: Subject to any disclaimer, the term of this patent is extended or adjusted under 35 U.S.C. 154(b) by 0 days.

(21) Appl. No.: 17/237,918

(22) Filed: Apr. 22, 2021

(65) Prior Publication Data
US 2021/0330081 A1  Oct. 28, 2021

Related U.S. Application Data

(60) Provisional application No. 63/015,210, filed on Apr. 24, 2020.

(51) Int. Cl.
  A47B 96/02    (2006.01)
  A47B 13/12    (2006.01)
  (Continued)

(52) U.S. Cl.
  CPC ............ A47B 96/027 (2013.01); A47B 96/06 (2013.01); A61L 2/10 (2013.01); A47B 13/12 (2013.01); A47B 2220/0075 (2013.01); A47B 2220/0077 (2013.01); A47F 3/001 (2013.01); A47F 5/0043 (2013.01); F21V 33/0012 (2013.01);
  (Continued)

(58) Field of Classification Search
  CPC ................... A61L 2/10; F21Y 2107/90; A47B 2220/0075; A47B 2220/0077; A47B 13/12; F25D 27/00; F25D 25/02; F25D 25/021; F25D 25/022; F25D 25/024; F25D 25/025; F25D 25/027; F25D 25/028;
  (Continued)

(56) References Cited

U.S. PATENT DOCUMENTS 3,506,325 A   4/1970  Horvay
4,973,796 A   11/1990 Dougherty et al.
(Continued)

FOREIGN PATENT DOCUMENTS

CN   1727748 A    2/2006
CN   201377735 Y  1/2010
(Continued)

OTHER PUBLICATIONS

Machine translation of KR 20190110972 A retrieved from the FIT database of PE2E search. (Year: 2023).*

(Continued)

*Primary Examiner* — Colin J Cattanach
(74) *Attorney, Agent, or Firm* — MARSHALL, GERSTEIN & BORUN LLP

(57) ABSTRACT

A shelf includes a shelf panel and an illumination module. The shelf panel has an upper surface, a lower surface, and an edge extending between the upper and lower surfaces. The upper surface is capable of supporting articles thereon. The illumination module is coupled to the shelf panel and includes a first plurality of lights emitting visible light when powered, and a second plurality of lights emitting light having a germicidal effect when powered.

7 Claims, 5 Drawing Sheets

(51) Int. Cl.
| | |
|---|---|
| *A47B 96/06* | (2006.01) |
| *A47F 3/00* | (2006.01) |
| *A47F 5/00* | (2006.01) |
| *A61L 2/10* | (2006.01) |
| *F21V 33/00* | (2006.01) |
| *F21W 131/301* | (2006.01) |
| *F21W 131/305* | (2006.01) |
| *F21Y 107/90* | (2016.01) |
| *F25D 25/02* | (2006.01) |
| *F25D 27/00* | (2006.01) |
| *G09F 3/20* | (2006.01) |

(52) U.S. Cl.
CPC . *F21W 2131/301* (2013.01); *F21W 2131/305* (2013.01); *F21Y 2107/90* (2016.08); *F25D 25/02* (2013.01); *F25D 25/021* (2013.01); *F25D 25/022* (2013.01); *F25D 25/024* (2013.01); *F25D 25/025* (2013.01); *F25D 25/027* (2013.01); *F25D 25/028* (2013.01); *F25D 27/00* (2013.01); *F25D 27/005* (2013.01); *G09F 3/204* (2013.01)

(58) Field of Classification Search
CPC ........ F21W 2131/301; F21W 2131/305; A47F 3/001; G09F 3/204
See application file for complete search history.

(56) References Cited

U.S. PATENT DOCUMENTS

| | | | |
|---|---|---|---|
| 5,034,861 A | 7/1991 | Sklenak et al. | |
| 5,287,252 A | 2/1994 | Caruso | |
| 5,403,083 A | 4/1995 | Dasher et al. | |
| 5,425,648 A | 6/1995 | Farham | |
| 5,429,433 A | 7/1995 | Bird et al. | |
| 5,454,638 A | 10/1995 | Bird et al. | |
| 5,564,809 A | 10/1996 | Kane et al. | |
| 5,690,415 A | 11/1997 | Krehl | |
| 5,735,589 A | 4/1998 | Herrmann et al. | |
| 5,745,514 A | 4/1998 | Patel et al. | |
| 6,042,244 A | 3/2000 | Witkoski | |
| 6,120,720 A | 9/2000 | Meier et al. | |
| 6,179,434 B1 | 1/2001 | Saraiji | |
| 6,210,013 B1 | 4/2001 | Bousfield | |
| 6,231,205 B1 | 5/2001 | Slesinger et al. | |
| 6,340,113 B1 | 1/2002 | Avery et al. | |
| 6,364,273 B1 | 4/2002 | Otema | |
| 6,431,721 B2 | 8/2002 | Shemitz et al. | |
| 6,558,017 B1 | 5/2003 | Saraiji et al. | |
| 6,578,979 B2 | 6/2003 | Truttmann-Battig | |
| 6,726,341 B2 | 4/2004 | Pashley et al. | |
| 6,786,562 B2 | 9/2004 | Obrock et al. | |
| 6,813,896 B1 | 11/2004 | Janke et al. | |
| 6,827,463 B2 | 12/2004 | Chuang et al. | |
| 7,005,805 B2 | 2/2006 | Ahn | |
| 7,080,920 B2 | 7/2006 | Fitzsimmons et al. | |
| 7,107,779 B2 | 9/2006 | Avenwedde et al. | |
| 7,121,675 B2 | 10/2006 | Ter-Hovhannisian | |
| 7,163,305 B2 | 1/2007 | Bienick | |
| 7,210,808 B2 | 5/2007 | Malpetti | |
| 7,273,299 B2 | 9/2007 | Parkyn et al. | |
| 7,338,180 B2 | 3/2008 | Wing | |
| 7,434,951 B2 | 10/2008 | Bienick | |
| 7,574,822 B1 * | 8/2009 | Moore .................... G09F 3/204 | |
| | | | 40/575 |
| 7,600,887 B2 | 10/2009 | Sherman | |
| 7,748,806 B2 | 7/2010 | Egan | |
| 7,766,502 B2 | 8/2010 | Tress | |
| 7,806,543 B2 | 10/2010 | Swofford et al. | |
| 7,824,055 B2 | 11/2010 | Sherman | |
| 7,840,286 B2 | 11/2010 | Caldwell et al. | |
| 7,976,181 B2 | 7/2011 | Kelly et al. | |
| 8,135,482 B2 | 3/2012 | Caldwell et al. | |
| 8,136,956 B2 | 3/2012 | Oketeni et al. | |
| 8,215,795 B2 | 7/2012 | Pichel | |
| 8,322,873 B2 | 12/2012 | Glovatsky et al. | |
| 8,360,802 B2 | 1/2013 | Allard et al. | |
| 8,453,476 B2 | 6/2013 | Kendall et al. | |
| 8,459,817 B2 | 6/2013 | Alberghetti et al. | |
| 8,678,616 B2 | 3/2014 | Marquardt et al. | |
| 8,944,621 B2 | 2/2015 | Driver et al. | |
| 8,967,740 B2 | 3/2015 | Kerner | |
| 8,979,296 B2 | 3/2015 | Wiemer et al. | |
| 9,098,823 B2 | 8/2015 | Slesinger et al. | |
| 9,157,678 B2 | 10/2015 | Kerner | |
| 9,287,021 B2 | 3/2016 | Hammond et al. | |
| 9,480,346 B2 | 11/2016 | Houle | |
| 9,595,373 B2 | 3/2017 | Hammond et al. | |
| 9,766,010 B2 | 9/2017 | Katu et al. | |
| 2003/0038571 A1 | 2/2003 | Obrock et al. | |
| 2003/0137828 A1 * | 7/2003 | Ter-Hovhannisian .... F21S 4/20 | |
| | | | 362/249.02 |
| 2004/0062031 A1 * | 4/2004 | Pinter .................. G02B 6/0095 | |
| | | | 362/330 |
| 2004/0212990 A1 | 10/2004 | Becker | |
| 2004/0264160 A1 * | 12/2004 | Bienick .................. F25D 27/00 | |
| | | | 362/23.15 |
| 2005/0093408 A1 | 5/2005 | Koloff et al. | |
| 2006/0029808 A1 | 2/2006 | Zhai et al. | |
| 2006/0216476 A1 | 9/2006 | Ganti et al. | |
| 2007/0058369 A1 | 3/2007 | Parkyn et al. | |
| 2007/0075199 A1 | 4/2007 | Stewart et al. | |
| 2007/0104841 A1 | 5/2007 | Min et al. | |
| 2007/0109764 A1 | 5/2007 | Bienick | |
| 2007/0127229 A1 | 6/2007 | Lee et al. | |
| 2007/0144196 A1 | 6/2007 | Currie | |
| 2007/0151274 A1 | 7/2007 | Roche et al. | |
| 2007/0180843 A1 | 8/2007 | Park et al. | |
| 2007/0266723 A1 | 11/2007 | Lee et al. | |
| 2008/0007945 A1 | 1/2008 | Kelly et al. | |
| 2008/0037239 A1 | 2/2008 | Thomas et al. | |
| 2008/0043456 A1 | 2/2008 | Bernardini et al. | |
| 2008/0092782 A1 | 4/2008 | Daniel | |
| 2008/0121146 A1 | 5/2008 | Burns et al. | |
| 2008/0158858 A1 | 7/2008 | Madireddi et al. | |
| 2008/0186695 A1 | 8/2008 | Awai et al. | |
| 2008/0186696 A1 | 8/2008 | Awai et al. | |
| 2008/0205044 A1 | 8/2008 | Shibusawa et al. | |
| 2008/0278932 A1 * | 11/2008 | Tress ...................... A47F 3/001 | |
| | | | 362/133 |
| 2009/0002990 A1 | 1/2009 | Becker et al. | |
| 2009/0021927 A1 | 1/2009 | Hall et al. | |
| 2009/0091271 A1 * | 4/2009 | Zulim .................... A47F 3/001 | |
| | | | 315/297 |
| 2009/0250715 A1 * | 10/2009 | Lee ...................... B08B 7/0057 | |
| | | | 257/E33.068 |
| 2010/0006519 A1 | 1/2010 | Van De Steen | |
| 2010/0097780 A1 | 4/2010 | Beatenbough et al. | |
| 2010/0135020 A1 | 6/2010 | Moore | |
| 2010/0195317 A1 | 8/2010 | Oketani | |
| 2010/0259148 A1 | 10/2010 | Alberghetti et al. | |
| 2011/0051401 A1 | 3/2011 | Bauer et al. | |
| 2011/0096533 A1 | 4/2011 | Sekela | |
| 2011/0164399 A1 | 7/2011 | Driver et al. | |
| 2011/0203302 A1 | 8/2011 | Alberghetti et al. | |
| 2011/0204009 A1 | 8/2011 | Karan | |
| 2011/0273867 A1 | 11/2011 | Horst et al. | |
| 2012/0106129 A1 * | 5/2012 | Glovatsky ............. F25D 23/067 | |
| | | | 362/92 |
| 2012/0230018 A1 | 9/2012 | Wiemer et al. | |
| 2013/0122739 A1 | 5/2013 | Allard et al. | |
| 2013/0188356 A1 | 7/2013 | Breslow et al. | |
| 2013/0286651 A1 | 10/2013 | Takeuchi | |
| 2014/0060095 A1 * | 3/2014 | Shur ...................... F25D 27/005 | |
| | | | 250/455.11 |
| 2014/0376213 A1 | 12/2014 | Miedema et al. | |
| 2015/0023000 A1 | 1/2015 | Kendall et al. | |
| 2015/0308653 A1 | 10/2015 | Wang et al. | |
| 2016/0097516 A1 * | 4/2016 | Howard .................. A47F 3/001 | |
| | | | 362/98 |
| 2017/0100495 A1 * | 4/2017 | Shur ...................... F25D 17/042 | |

(56) References Cited

U.S. PATENT DOCUMENTS

| | | | |
|---|---|---|---|
| 2017/0368215 A1* | 12/2017 | Shatalov | H04N 5/332 |
| 2018/0221521 A1* | 8/2018 | Shur | A61L 2/10 |
| 2018/0243458 A1* | 8/2018 | Shatalov | A61L 9/20 |
| 2018/0306971 A1* | 10/2018 | Conrad | F21K 9/61 |

FOREIGN PATENT DOCUMENTS

| | | | | |
|---|---|---|---|---|
| CN | 101791180 A | | 8/2010 | |
| CN | 201875445 U | | 6/2011 | |
| CN | 201977332 U | | 9/2011 | |
| CN | 201999332 U | | 10/2011 | |
| CN | 102656404 A | | 9/2012 | |
| CN | 202504813 U | | 10/2012 | |
| CN | 102980089 A | | 3/2013 | |
| CN | 202886235 U | | 4/2013 | |
| CN | 103104892 A | | 5/2013 | |
| CN | 107192213 A | | 9/2017 | |
| DE | 202009010551 U1 | | 12/2009 | |
| DE | 202010005347 U1 | | 8/2010 | |
| DE | 102009002503 A1 | | 10/2010 | |
| DE | 202009018504 U1 | | 12/2011 | |
| DE | 102015007839 A1 | * | 12/2016 | F21V 33/00 |
| EP | 1174661 A1 | | 1/2002 | |
| EP | 1222885 A1 | | 7/2002 | |
| EP | 1503159 A2 | | 2/2005 | |
| EP | 1887299 A2 | | 2/2008 | |
| EP | 1961340 A1 | | 8/2008 | |
| EP | 2161496 A1 | | 3/2010 | |
| EP | 3558305 A1 | | 10/2019 | |
| JP | 2002313133 A | | 10/2002 | |
| JP | 2004081521 A | | 3/2004 | |
| JP | 2004344507 A | | 12/2004 | |
| JP | 2010170970 A | | 8/2010 | |
| JP | 2010182520 A | | 8/2010 | |
| JP | 2010264226 A | | 11/2010 | |
| JP | 2012040334 A | | 3/2012 | |
| KR | 200343464 Y1 | | 3/2004 | |
| KR | 787552 B1 | * | 12/2007 | G02B 6/003 |
| KR | 20110034271 A | | 4/2011 | |
| KR | 20190110972 A | * | 10/2019 | |
| WO | WO-2006126584 A1 | * | 11/2006 | A61L 2/10 |
| WO | WO-2007020470 A1 | | 2/2007 | |
| WO | WO-2013034497 A1 | | 3/2013 | |

OTHER PUBLICATIONS

Machine translation of WO-2006126584-A1 retrieved from the FIT database of PE2E search. (Year: 2023).*
International Application No. PCT/US2022/046373, International Search Report and Written Opinion, mailed Feb. 16, 2023.
International Application No. PCT/US2022/046381, International Search Report and Written Opinion, mailed Jan. 20, 2023.
International Application No. PCT/US2022/046376, International Search Report and Written Opinion of the International Searching Authority, mailing date Jan. 20, 2023.
Chinese Patent Application No. 202010870105.8, First Office Action, dated Mar. 29, 2022.
International Search Report dated Oct. 31, 2014 for PCT application No. PCT/US2014/43418, 3 pages.
Written Opinion dated Oct. 31, 2014 for PCT application No. PCT/US2014/43418, 6 pages.
International Preliminary Report on Patentability dated Dec. 22, 2015 for corresponding International Patent Application No. PCT/US2014/43418, 7 pages.

* cited by examiner

ILLUMINATED SHELF

CROSS-REFERENCE TO RELATED APPLICATION

Priority is claimed to U.S. Provisional Patent Application No. 63/015,210, filed Apr. 24, 2020, the entire contents of which are hereby incorporated herein by reference.

FIELD OF THE DISCLOSURE

The present disclosure is related to shelves and, more particularly, appliance shelves such as refrigerator shelves.

BACKGROUND

Enclosures and appliances contain shelves and similar storage devices within the appliance interior to organize and support stored goods such as food and containers. These shelves and similar storage devices can be made from a variety of materials including glass, plastic, wood and metals, such as wire and sheet steel. In refrigerators, for example, some known shelving solutions include a glass shelf panel resting on a pair of cantilever sideplate brackets that engages into corresponding features at the back of the refrigerator cavity. The front edge of the glass panel can be exposed or can include a trim piece for aesthetic purposes, and also to provide a softer edge for absorbing shocks from containers being placed into the refrigerator. Similarly, the rear edge of the glass panel can be exposed or can include a rear trim component that is slightly raised above the top surface of the glass shelf to act as a stopper or bumper preventing items from falling off the back of the shelf. Some examples of such products are discussed in the literature including, for example, U.S. Pat. Nos. 4,736,997, 4,923,260, 5,332,611, 8,684,479, and 8,850,839.

Goods ultimately disposed on shelves may come into contact with germs during transportation and/or during storage. Additionally, the goods disposed on the shelves within an enclosure have a point after which they no longer contain the same amount of nutrients and/or a point after which they are no longer viable to be consumed (e.g., expiration date). After the expiration date, germs may begin to form on the goods (e.g., mold). In some cases, the germs may be visible immediately or after a certain period of time, which may visually indicate to a user that the good is no longer viable for consumption. However, such germ formation may not be readily visible by the human eye. As a result, germs may spread from the particular good to other goods in close proximity to the particular good and/or to the shelf that the particular good is disposed on. The spread of such germs may not only be detrimental to the health of the individual consuming the good, but may also result in countless dollars lost by the purchaser of the good because the good must be disposed of as a result of the germ growth. This invention seeks to help provide an improvement to food preservation, food waste and visibility of stored products.

SUMMARY

One aspect of the present disclosure includes a shelf having a shelf panel and an illumination module. The shelf panel has an upper surface, a lower surface, and an edge extending between the upper and lower surfaces. The upper surface is capable of supporting articles thereon. The illumination module is coupled to the shelf panel and includes a first plurality of lights emitting visible light when powered, and a second plurality of lights emitting light having a germicidal effect when powered.

In some aspects, the shelf further includes a trim component releasably coupled to the illumination module of the shelf panel.

In some aspects, the illumination module is selectively operable between (a) a first configuration, where the first plurality of lights receives power to visibly illuminate the shelf panel and/or the trim component, and (b) a second configuration, where the second plurality of lights receives power to emit germicidal light toward at least one of the shelf panel, the trim component or areas adjacent to the shelf panel, thereby reducing and/or eliminating germs disposed on at least one of the shelf panel, the trim component or areas adjacent to the shelf panel.

In some aspects, the second plurality of lights emit light having a wavelength between 100 and 470 nanometers (nm).

In some aspects, the second plurality of lights comprise (a) lights emitting UVA light having a wavelength between 315 nm and 400 nm, (b) lights emitting UVB light having a wavelength between 280 nm and 315 nm, (c) lights emitting UVC light having a wavelength between 100 nm and 280 nm, and/or (d) blue LEDs emitting light having a wavelength between 400 nm and 470 nm.

In some aspects, the first plurality of lights emit white light or other visible spectrum color.

In some aspects, the illumination module comprises a third plurality of lights generating visible light when powered, and wherein, in the first configuration, the third plurality of lights receives power to visibly illuminate the shelf panel and/or the trim component.

In some aspects, in the second configuration, the second plurality of lights intermittently receives power.

In some aspects, the illumination module further comprises a housing adapted to receive at least one of the pluralities of lights and a lens received by the housing such that at least one of the pluralities of lights is disposed between the lens and the housing.

In some aspects, the housing includes at least one leg in engagement with either the upper surface of the shelf panel or with the lower surface of the shelf panel.

In some aspects, the trim component includes a face and at least one securing arm extending from the face, the face having at least one transparent portion such that light can pass through the at least one transparent portion.

In some aspects, the at least one transparent portion is disposed on the face of the trim component such that the at least one transparent portion forms and/or comprises an emblem, a brand logo, a product name, or a universal product code (UPC).

In some aspects, the at least one securing arm comprises: a leg portion extending from the face of the trim component; and an engagement portion extending from the leg portion, the engagement portion configured to releasably couple the trim component to the housing of the illumination module.

In some aspects, the trim component is releasably coupled to the illumination module via a snap-fit, friction fit, magnetic fit or Velcro fit.

In some aspects, the first plurality of lights emits light in a first direction such that the first plurality of lights illuminates the edge of the shelf panel, above the edge of the shelf panel, and/or below the edge of the shelf panel.

In some aspects, the shelf further includes at least one support bracket coupled to the shelf panel, the at least one support bracket configured to couple the shelf panel to the enclosure.

In some aspects, the shelf further includes a power supply configured to provide power to the illumination module In some aspects, the power supply is at least one battery disposed within the illumination module.

In some aspects, the power supply is coupled to the shelf panel.

In some aspects, the illumination module is operably coupled to an electrical circuit of an appliance.

A second aspect of the present disclosure includes a shelf including a shelf panel, an illumination module and a trim component. The shelf panel has an upper surface, a lower surface, and an edge extending between the upper and lower surfaces. The upper surface is capable of supporting articles thereon. The illumination module includes a first plurality of lights emitting visible light when powered. The trim component releasably couples to the illumination module of the shelf panel.

In some aspects, the illumination module is selectively operable between (a) a first configuration, where the first plurality of lights receives power to visibly illuminate the shelf panel and/or the trim component, and (b) a second configuration, where the first plurality of lights receives no power.

In some aspects, the illumination module further comprises a second plurality of lights emitting light having a germicidal effect when powered.

In some aspects, the illumination module is selectively operable between (a) a first configuration, where the first plurality of lights receives power to visibly illuminate the shelf panel and/or the trim component, and (b) a second configuration, where the second plurality of lights receives power to emit germicidal light toward at least one of the shelf panel and the trim component, thereby reducing and/or eliminating germs disposed on at least one of the shelf panel, the trim component or areas adjacent to the shelf panel.

In some aspects, the second plurality of lights emit light having a wavelength between 100 and 470 nanometers (nm).

In some aspects, the second plurality of lights comprise (a) lights emitting UVA light having a wavelength between 315 nm and 400 nm, (b) lights emitting UVB light having a wavelength between 280 nm and 315 nm, (c) lights emitting UVC light having a wavelength between 100 nm and 280 nm, and/or (d) blue LEDs emitting light having a wavelength between 400 nm and 470 nm.

In some aspects, the first plurality of lights emit white light or other visible spectrum color.

In some aspects, the illumination module comprises a third plurality of lights generating visible light when powered, and wherein, in the first configuration, the third plurality of lights receives power to visibly illuminate the shelf panel and/or the trim component.

In some aspects, in the second configuration, the second plurality of lights intermittently receives power.

In some aspects, the illumination module further comprises a housing adapted to receive at least one of the pluralities of lights and a lens received by the housing such that at least one of the pluralities of lights is disposed between the lens and the housing.

In some aspects, the housing includes at least one leg in engagement with either the upper surface of the shelf panel or with the lower surface of the shelf panel.

In some aspects, the trim component includes a face and at least one securing arm extending from the face, the face having at least one transparent portion such that light can pass through the at least one transparent portion.

In some aspects, the at least one transparent portion is disposed on the face of the trim component such that the at least one transparent portion forms and/or comprises an emblem, a brand logo, a product name, or a universal product code (UPC).

In some aspects, the at least one securing arm comprises: a leg portion extending from the face of the trim component; and an engagement portion extending from the leg portion, the engagement portion configured to releasably couple the trim component to the housing of the illumination module.

In some aspects, the trim component is releasably coupled to the illumination module via a snap-fit, friction fit, magnetic fit or Velcro fit.

In some aspects, the first plurality of lights emits light in a first direction such that the first plurality of lights illuminates the edge of the shelf panel, above the edge of the shelf panel, and/or below the edge of the shelf panel.

In some aspects, the shelf further includes at least one support bracket coupled to the shelf panel, the at least one support bracket configured to couple the shelf panel to the enclosure.

In some aspects, the shelf further includes a power supply configured to provide power to the illumination module In some aspects, the power supply is at least one battery disposed within the illumination module.

In some aspects, the power supply is coupled to the shelf panel.

In some aspects, the illumination module is operably coupled to an electrical circuit of an appliance.

A third aspect of the present disclosure includes a shelf having a shelf panel, at least one support bracket, an illumination module and (a) a second plurality of lights and/or (b) a trim component. The shelf panel has an upper surface, a lower surface, and an edge that extends between the upper and lower surfaces. The upper surface is capable of supporting articles thereon. The at least one support bracket is coupled to the storage surface and configured to couple the shelf panel to the enclosure. The illumination module includes a first plurality of lights emitting visible light when powered. The (a) a second plurality of lights is part of the illumination module and has a germicidal effect when powered. The (b) a trim component is releasably coupled to the illumination module of the shelf panel.

In some aspects, the illumination module is selectively operable between (a) a first configuration, where the first plurality of lights receives power thereby illuminating the shelf panel and/or trim component, and (b) a second configuration, where the first plurality of lights receives no power.

In some aspects, the illumination module is selectively operable between (a) a first configuration, where the first plurality of lights receives power thereby illuminating the shelf panel and/or trim component, and (b) a second configuration, where the second plurality of lights receives power to emit germicidal light toward at least one of the shelf panel, the trim component or areas adjacent to the shelf panel, thereby reducing and/or eliminating germs disposed on at least one of the shelf panel, the trim component or areas adjacent to the shelf panel.

In some aspects, the second plurality of lights emit light having a wavelength between 100 and 470 nanometers (nm).

In some aspects, the second plurality of lights comprise (a) lights emitting UVA light having a wavelength between 315 nm and 400 nm, (b) lights emitting UVB light having a wavelength between 280 nm and 315 nm, (c) lights emitting UVC light having a wavelength between 100 nm and 280 nm, and/or (d) blue LEDs emitting light having a wavelength between 400 nm and 470 nm.

In some aspects, the first plurality of lights emit white light or other visible spectrum color.

In some aspects, the illumination module includes a third plurality of lights having a third wavelength that is different from the first wavelength, and wherein, in the first configuration, the third plurality of lights receives power thereby illuminating the trim component.

In some aspects, in the second configuration, the second plurality of lights intermittently receives power.

In some aspects, the illumination module further comprises a housing adapted to receive at least one of the pluralities of lights and a lens received by the housing such that at least one of the pluralities of lights are disposed between the lens and the housing.

In some aspects, the housing includes at least one leg in engagement with either the upper surface of the shelf panel or with the lower surface of the shelf panel.

In some aspects, the trim component includes a face and at least one securing arm extending from the face, the face having at least one transparent portion such that light can pass through the at least one transparent portion.

In some aspects, the at least one transparent portion is disposed on the face of the trim component such that the at least one transparent portion forms and/or comprises an emblem, a brand logo, a product name, or a universal product code (UPC).

In some aspects, the at least one securing arm comprises: a leg portion extending from the face of the trim component; and an engagement portion extending from the leg portion, the engagement portion configured to releasably couple the trim component to the housing of the illumination module.

In some aspects, the trim component is releasably coupled to the illumination module via a snap-fit, friction fit, magnetic fit or Velcro fit.

In some aspects, the first plurality of lights emits light in a first direction such that the first plurality of lights illuminates the edge of the shelf panel, above the edge of the shelf panel, and/or below the edge of the shelf panel.

In some aspects, the shelf further includes a power supply configured to provide power to the illumination module.

In some aspects, the power supply is at least one battery disposed within the illumination module.

In some aspects, the power supply is coupled to the shelf panel.

In some aspects, the illumination module is operably coupled to an electrical circuit of an appliance.

DETAILED DESCRIPTION

A shelf assembly for a temperature-controlled enclosure (e.g., a refrigerator) described herein is capable of illuminating products disposed on the shelf assembly to both aid individuals in viewing the products disposed thereon and reduce, or eliminate entirely, germs including bacteria, viruses and fungi disposed on the stored products, shelf assembly, and/or other items within the enclosure. By providing such a shelf assembly, the illumination module may include several lights emitting light at two or more different wavelengths to achieve different objectives including disinfection and increased visibility. Advantageously, the lights may be oriented in several different directions so that the illumination module may emit light in several different directions as desired.

Figure 1:
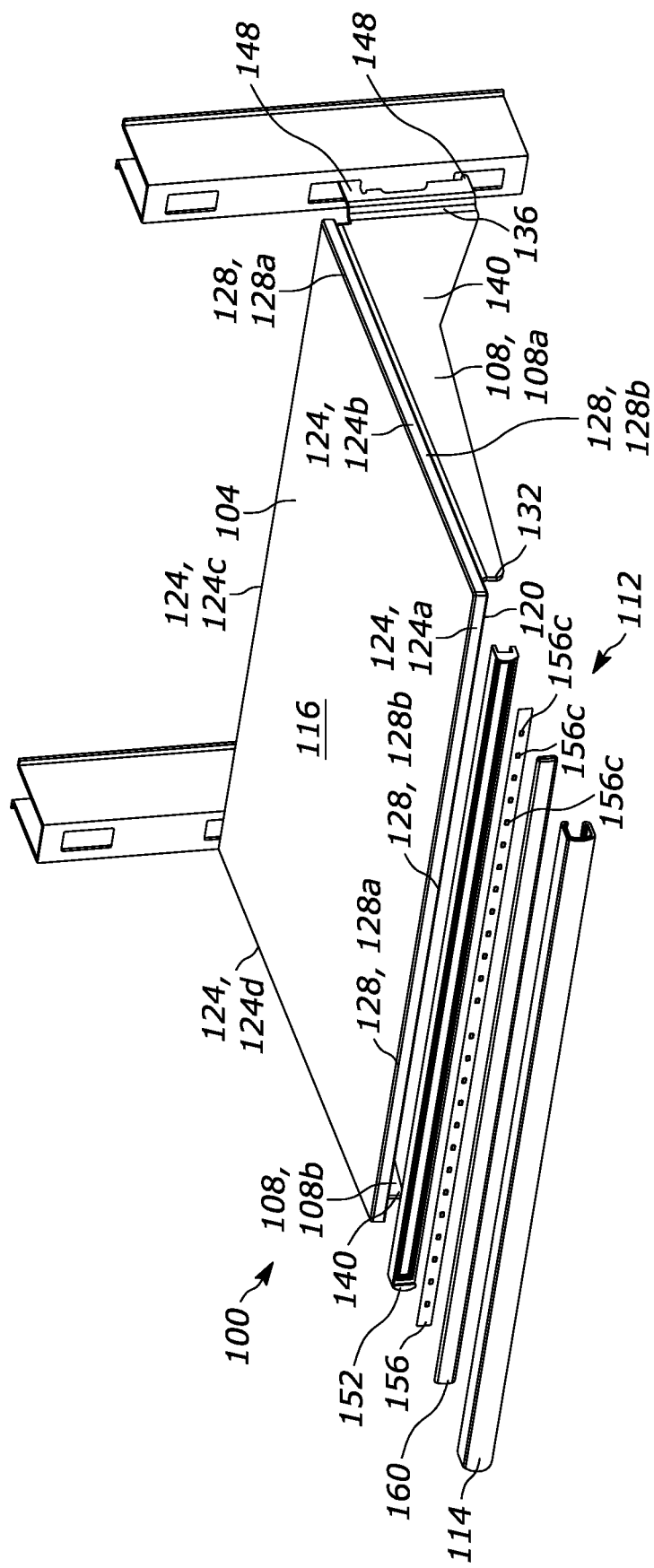
FIG. 1 illustrates a front perspective view of an example shelf for a temperature-controlled enclosure, for example, with an illumination module, the illumination module shown exploded.
Figure 2:
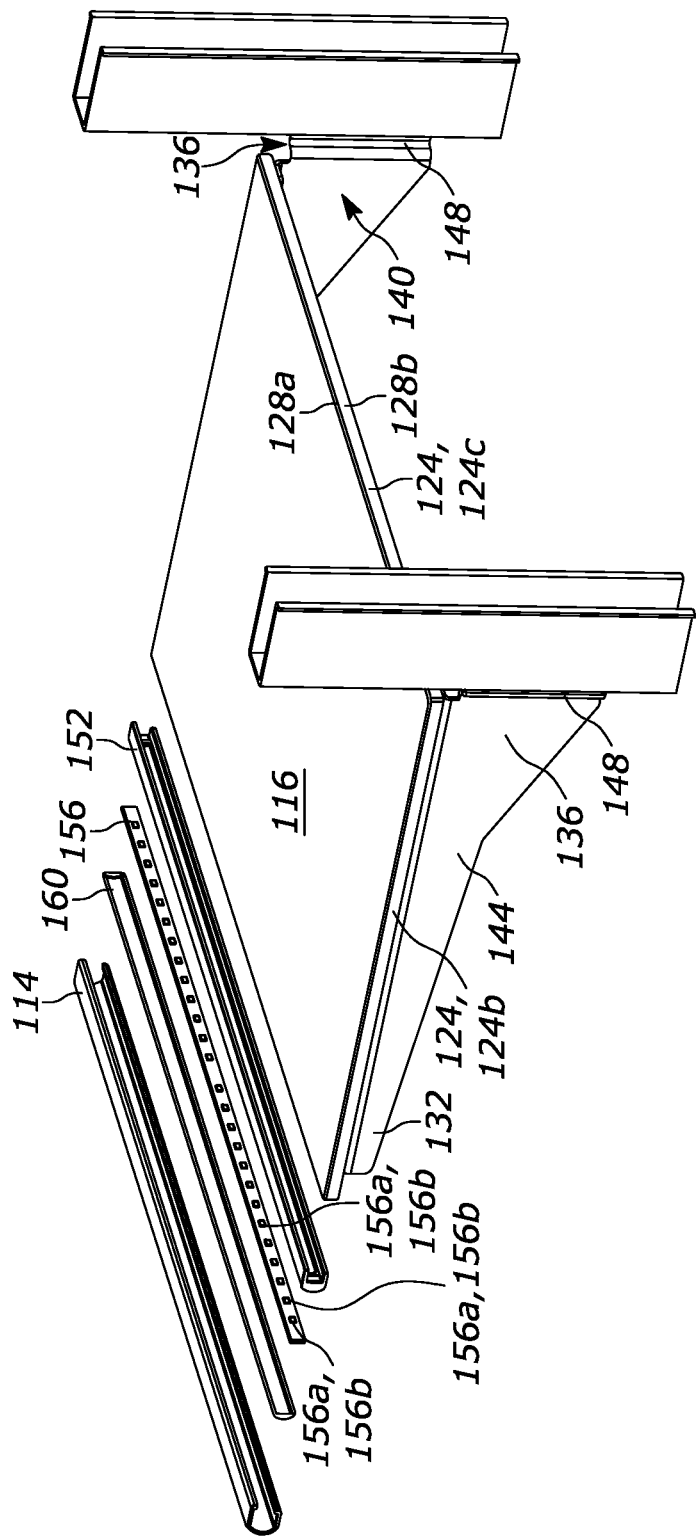
FIG. 2 illustrates a rear perspective view of the shelf of FIG. 1.
Figure 3:
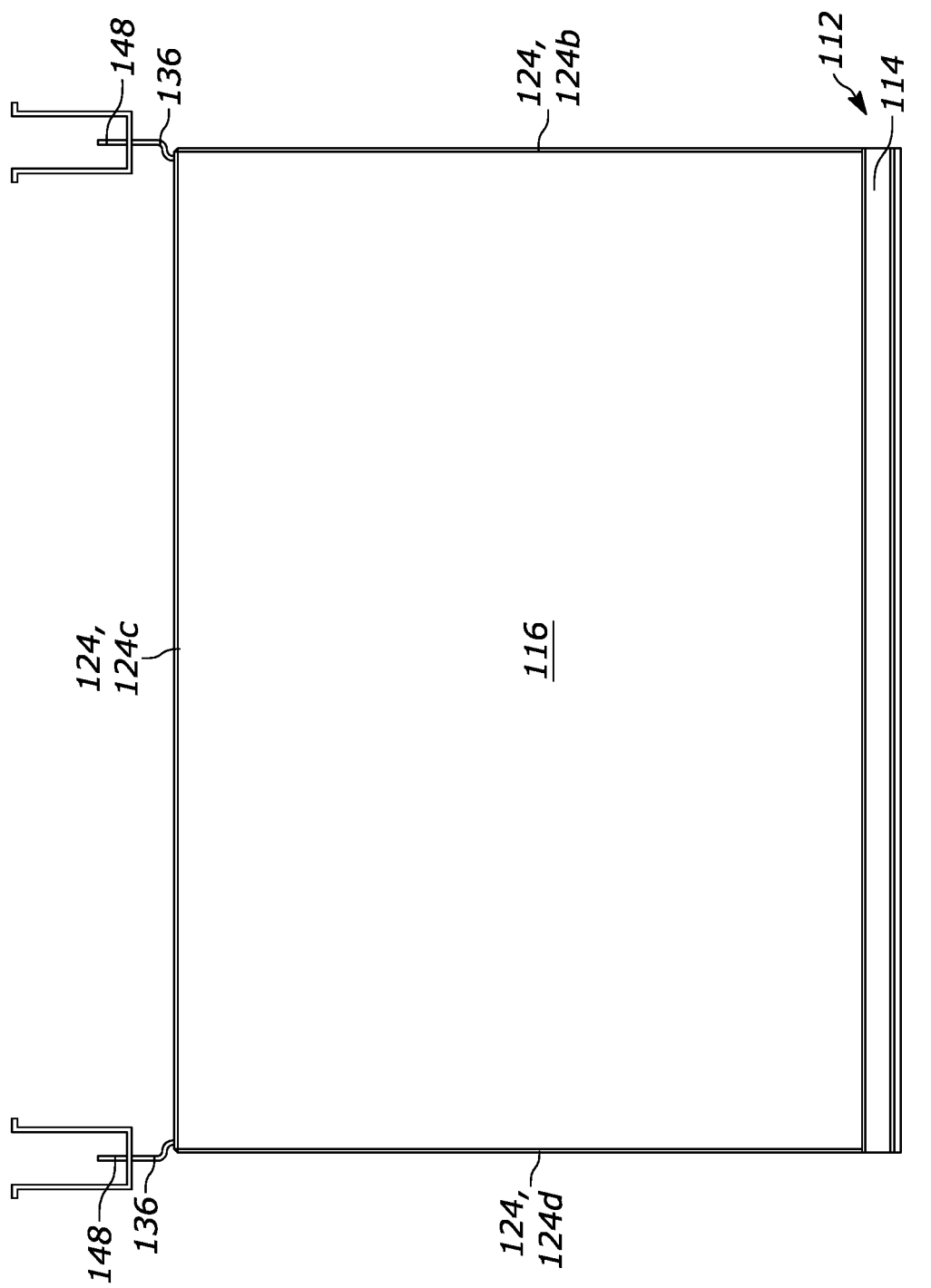
FIG. 3 illustrates a top view of the shelf of FIG. 1.
Figure 4:
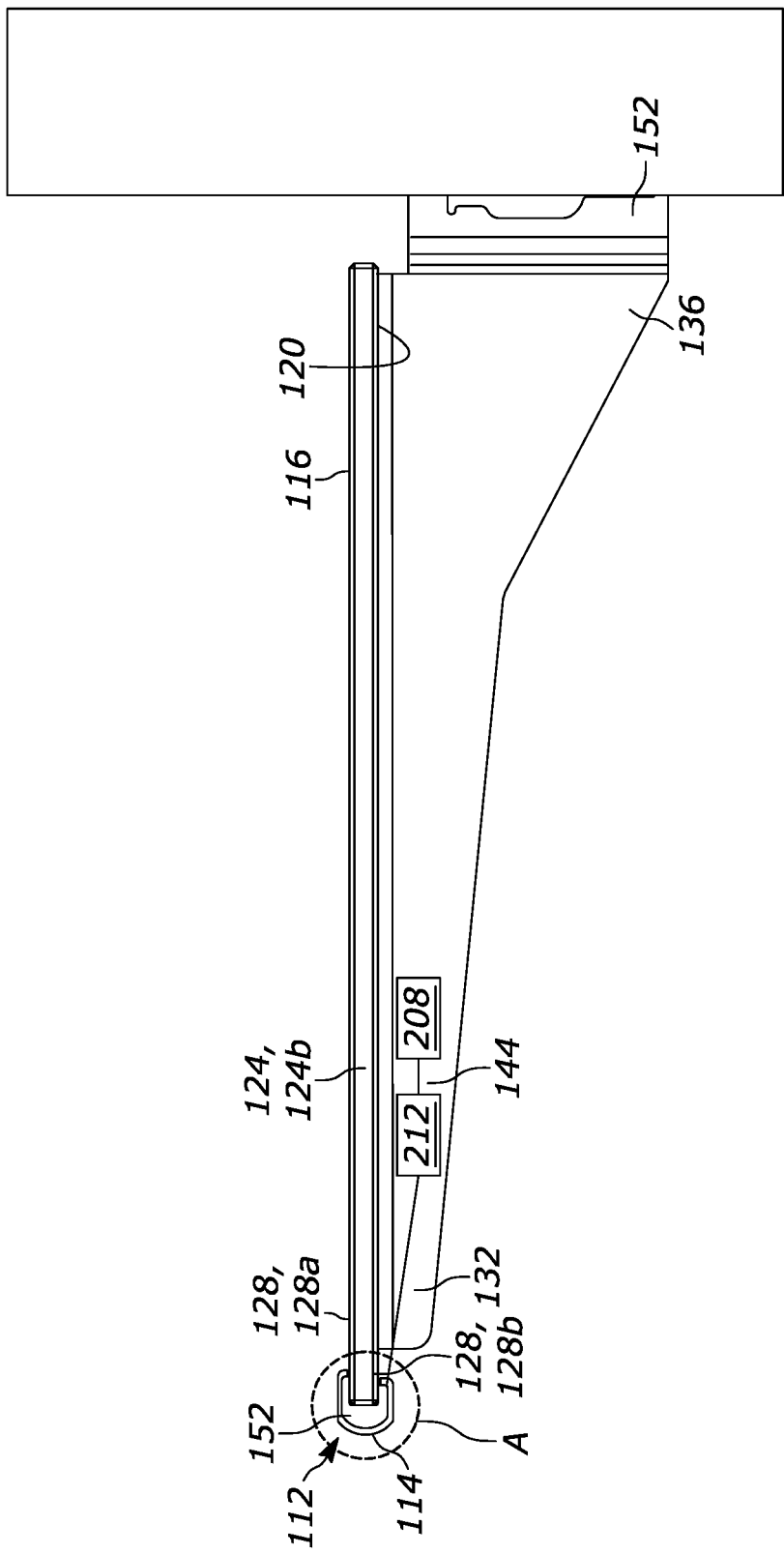
FIG. 4 illustrates a side view of the shelf of FIG. 1.

FIGS. 1-4 illustrate an example of the disclosed shelf assembly 100. In particular, FIG. 1 illustrates a front perspective view of the shelf assembly 100; FIG. 2 illustrates a rear perspective view of the shelf assembly 100; FIG. 3 illustrates a top view of the shelf assembly 100; and FIG. 4 illustrates a side view of the shelf assembly 100. The shelf assembly 100 may be used in enclosures or temperature-controlled enclosures such as, for example, a residential or commercial refrigerator, a freezer, a wine cooler, a multi-deck commercial refrigerator unit, serve over counter unit, an upright glass door refrigerator, a patisserie display unit, a walk-in enclosure, or any other enclosure temperature controlled or otherwise.

In general, the shelf 100 includes a shelf panel 104, a support frame 108, an illumination module 112, and a trim component 114 coupled to the illumination module 112 used with the shelf panel 104. The shelf panel 104 includes a generally flat and planar article having an upper surface 116, a lower surface 120 that is opposite the upper surface 126, and an edge 124 that extends between the upper surface 116 and the lower surface 120. In particular, because the shelf panel 104 includes a generally uniform thickness, there is a first edge 124*a*, a second edge 124*b*, a third edge 124*c*, and a fourth edge 124*d* disposed at respective sides of the shelf panel 104 between the upper and lower surfaces 116, 120. The shelf panel 104 also may optionally include a plurality of bevels 128 along the edge 124. In particular, a first bevel 128*a* of the plurality of bevels 128 may be disposed between the upper surface 116 and the first, second, third, and fourth edges 124*a-d*, and a second bevel 128*b* disposed between the lower surface 120 and the first, second, third, and fourth edges 124*a-d*.

The shelf panel 104 of the depicted version may be a uniform surface, as illustrated in FIGS. 1-4, made of glass, metal, plastic, or any other polymer. In other examples, however, the shelf panel 104 can be a welded wireform mat. Additionally, while the shelf panel 104 is described and illustrated as including the plurality of bevels 128, other examples of the shelf panel 104 can include a chamfer or not include a bevel at all.

As illustrated in FIGS. 1 and 2, the support frame 108 releasably couples the shelf panel 104 to a portion of the enclosure, such as, for example, a ladder rack type assembly (shown partly in FIG. 1), in a cantilevered fashion, as conventionally known in the appliance industry. As illustrated in FIGS. 1 and 2, the support frame 108 includes a first sideplate bracket 108*a* and a second sideplate bracket 108*b*. Each of the first and second sideplate brackets 108*a*, 108*b* includes a front end 132, a rear end 136 that is opposite the front end 132, an inner portion 140, and an outer portion 144 that is opposite the inner portion 140. The first and second sideplate brackets 108*a*, 108*b* may be a stamped metal. In other examples, the first and second sideplate brackets 108*a*, 108*b* can be formed of wire or any other conductive, or non-conductive material. The rear end 136 includes a hook 148 for mounting into the ladder rack type assembly disposed on a portion of the enclosure. In other examples, however, the first and second sideplate brackets 108*a*, 108*b* can be secured to a portion of the enclosure using a mechanical fastener, an adhesive, a tape bond, an ultrasonic weld, a snap fit, or any other known attachment mechanisms. In still other versions, the shelf 100 does not include sideplate brackets 108 at all, but rather, the shelf panel 104 may be directly supported on ribs or other structures formed directly on or otherwise supported by the side walls of the associated enclosure in which the shelf 100 resides.

As discussed above, products disposed on the shelf panel 104 may have naturally occurring germs that exist during the time of initial storage or that form after the product has been disposed in the enclosure for a certain period of time (e.g., after the expiration date of the product). Additionally, the germs found on one product may be transferred to other products disposed on the shelf panel 104 and/or the shelf panel 104 itself simply because the product is disposed near another product on the shelf panel 104. Concerns with germs become further exacerbated upon the occurrence of food and/or drink spills occurring in the enclosure. Problematically, formation of the germs may occur without any visual indication to the user before the germs reaches a very advanced stage of growth. It is therefore desirable to mitigate and/or eliminate the growth and spread of such germs for the health and safety of individuals accessing the enclosure and/or consuming the products disposed on the shelf panel 104. Exposing the products to certain lights (i.e., certain wavelengths of light) helps to mitigate and/or eliminate the growth of germs disposed on the products, the shelf panel 104 and/or within the enclosure itself. Advantageously, the described illumination module 112 emits light on the products disposed on the shelf panel 104, the shelf panel 104 itself and/or adjacent shelves, products, storage drawers, bins or other specific targeted areas as desired within the enclosure for mitigating and/or eliminating germ growth.

Figure 5:
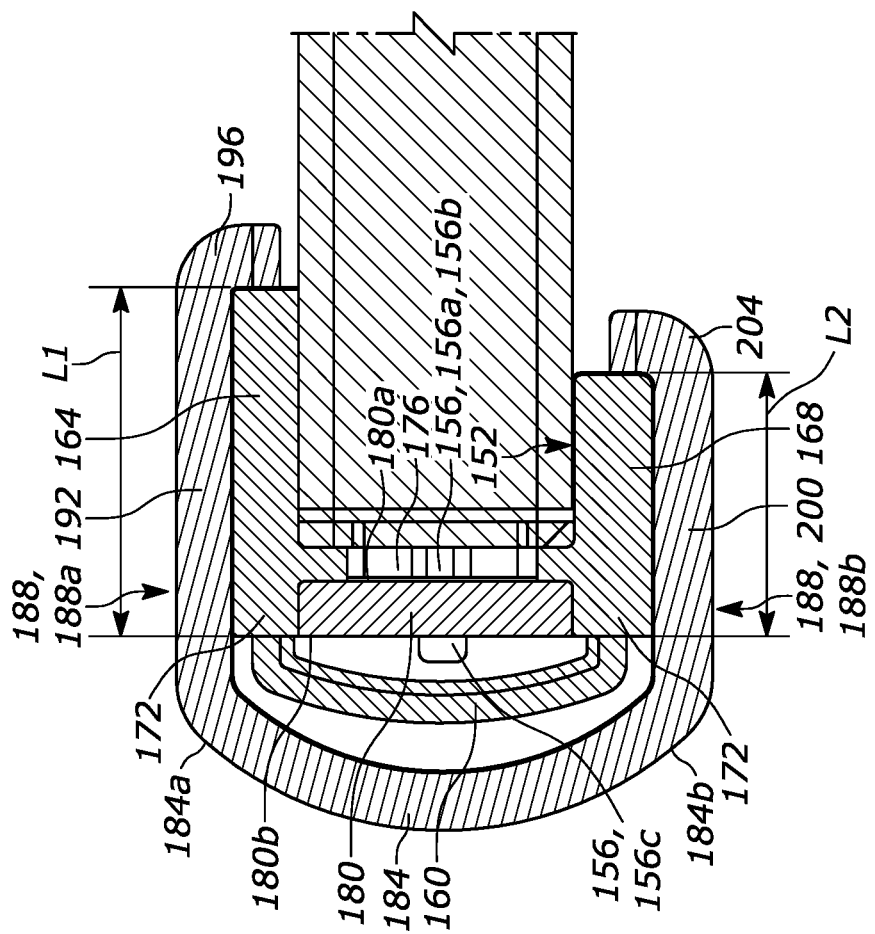
FIG. 5 illustrates a detailed side view of the illumination module of FIG. 4 within circle A.

As illustrated in FIGS. 3-5, the illumination module 112 is coupled to the first edge 124a of the shelf panel 104. However, in other examples, an illumination module 112 can be coupled to the second, third, and/or fourth edges 124b-d depending on the configuration of the enclosure, the configuration of the shelf panel 104, and/or other desire. In general, and as can be seen in FIG. 2, the illumination module 112 includes a housing 152 operably coupled to the shelf panel 104, a set of lights 156 coupled to the housing 152, and a lens 160 operably coupled to the set of lights 156 and the housing 152. In particular, as best illustrated in FIGS. 4 and 5, the housing 152 includes a first leg 164 in engagement with the upper surface 116 of the shelf panel 104 and a second leg 168 in engagement with the lower surface 120 of the shelf panel 104. As best illustrated in FIG. 5, the first leg 164 includes a first length L1 and the second leg 168 includes a second length L2 that is different from the first length L1. In other examples, however, the first length L1 can be less than the second length L2, the first length L1 and second length L2 can be substantially equal to each other or other housing profiles with or without first and/or second legs may be utilized. The first and second legs 164, 168 may be in frictional engagement with the upper and lower surfaces 116, 120, respectively, of the shelf panel 104 as illustrated. In other examples, however, the first and second legs 164, 168 can be coupled to the upper, side and lower surfaces 120 of the shelf panel 104 using an adhesive, a snap fit, a tongue and groove, Velcro, magnets or any other mechanical attachment mechanism or adhesive.

Further, the housing 152 includes a lip 172 that is adapted to receive and hold the set of lights 156 and an opening 176 disposed through the housing 152 and proximate the set of lights 156 such that light emitted from the set of lights 156 may pass through the opening 176 back toward the shelf panel 104. In particular, a portion of the first leg 164 and a portion of the second leg 168 forms the lip 172 that is adapted to receive and hold the set of lights 156. The lip 172 may extend along the entirety of the housing 152 to securely retain the set of lights 156. In particular, the lip 172 may receive the set of lights 156 such that the lip 172 and set of lights 156 are in frictional engagement. In other examples, however, the lip 172 can securely receive the set of lights 156 via snap-fit, adhesive, hook and loop, or any other mechanical coupling mechanism. Additionally, in some examples, the lip 172 can extend along a portion of the housing such that the lip 172 receives the set of lights 156 at particular locations on the housing 152.

The opening 176 is disposed through the housing 152 and positioned relative to the set of lights 156 such that light emitted from the set of lights 156 passes through the opening 176 back toward the shelf panel 104 and, more particularly, toward the first edge 124a of the shelf panel 104 upon which the illumination module 112 is mounted. As best illustrated in FIG. 5, the opening 176 may be disposed centrally through the housing 152 such that the opening 176 aligns with the set of lights 156. The opening 176 may be an elongated opening that extends from a point located near a first end of the housing 152 to another point located near a second end of the housing 152 that is opposite the first end. In other examples, however, the opening 176 can instead be several individual openings that are disposed along the length of the housing 152. In such an example, each opening disposed through the housing 152 can be aligned with the set of lights 156 such that each opening permits each light in the set of lights 156 to emit light therethrough.

The housing 152 described may be made of any suitable material capable of frictionally engaging other structures. For example, the housing 152 can be constructed of an elastomer that facilitates frictional engagement such as rubber. Because the housing 152 may engage other structures via a snap-fit, the housing 152 may be constructed of a rigid material capable of deforming enough to pass over the structure but capable of returning to the original form of the housing 152. For example, the housing 152 can be constructed of a polymer.

The set of lights 156 received by the housing 152 includes several different lights each optionally capable of emitting a different wavelength of light. In particular, the set of lights 156 includes a first plurality of lights 156a configured to emit a first wavelength of light and a second plurality of lights 156b configured to emit a second wavelength of light that is different from the first wavelength of light. The set of lights 156 may also include a third plurality of lights 156c that is configured to emit a third wavelength of light that may be the same as or different from the first light and/or the second light.

For example in one version, the first and third pluralities of lights 156a, 156c may be capable of emitting first and third wavelengths of light including a visible light that illuminates the products disposed on the shelf panel 104, products disposed adjacent to the shelf panel 104, the shelf panel 104 itself and/or as desired within the enclosure. In contrast, the second wavelength emitted by the second plurality of lights 156b may be a wavelength capable of reducing and/or eliminating germs on the products disposed on the shelf panel 104, the shelf panel 104 itself and/or adjacent shelves, products, storage drawers, bins or other specific targeted areas as desired within the enclosure. Despite the spectrum of visible and ultra-violet light being broad, certain germs may be more sensitive to certain types of light within the spectrum. It has been determined, for example, that certain germs can be reduced and or eliminated when exposed to blue light, or light in the wavelength of 400-470 nanometers ("nm"); when exposed to ultraviolet-A ("UV-A") light, which is ultraviolet light having a wavelength in the range from 315-400 nm; when exposed to ultraviolet-B ("UV-B") light, which is ultraviolet light having a wavelength in the range from 280-315 nm; and/or reduced and/or eliminated when exposed to ultraviolet C ("UV-C") light, which is ultraviolet light having a wavelength in the range from 100-280 nm. It is therefore desirable that the second plurality of lights be capable of emitting light that has a germicidal effect such as at least one of blue light generated from blue LEDs, UV-A, UV-B, and/or UV-C.

While the second plurality of lights 156*b* is configured to emit a germicidal light capable of reducing and/or eliminating germs disposed on the products or directed to other areas within the enclosure, such light may not be capable of and/or effective at visibly illuminating the products disposed on the shelf panel 104 and/or the shelf panel 104 itself. As such, it is desirable that the illumination module 112 be configured to also emit a light that is capable of visibly illuminating the products disposed on the shelf panel 104, products disposed adjacent to the shelf panel 104 or as desired within the enclosure.

As discussed above, the first plurality of lights 156*a* emits light having a first wavelength and the third plurality of lights 156*c* emits light having a third wavelength. In particular, the first and third wavelengths of light emitted by the first plurality of lights 156*a* and the third plurality of lights 156*c*, respectively, are different than the second wavelength of lights. For example, the first and third wavelengths can include white light or other light in the visible spectrum. Further, the first and third wavelengths of light may be the same wavelength. In such an example, the first and third pluralities of lights 156*a*, 156*c* can illuminate the products disposed on the shelf panel 104 and/or the shelf panel 104 itself evenly (i.e., the same intensity and the same spectrum). In other examples, however, the first and third wavelengths can be different wavelengths emitted at different intensities.

In addition to the first, second, and third pluralities of lights 156*a-c* being configured to emit different wavelengths of light, the first, second, and third pluralities of lights 156*a-c* are oriented to emit light in various directions relative to the shelf panel 104. In particular, the first plurality of lights 156*a* may also be oriented in a first direction relative to the shelf panel 104 such that the light emitted from the first plurality of lights 156*a* is directed toward the product(s) disposed on the shelf panel 104 and/or an area adjacent to the shelf panel 104. In particular, the first direction may be oriented relative to the shelf panel 104 such that the first plurality of lights 156*a* emits a light toward at least one of the edge 124*a-d* of the shelf panel 104, across and/or above the upper surface 116 of the shelf panel 104, or across and/or below the lower surface 120 of the shelf panel 104. If, for example, the first plurality of lights 156*a* emits light toward the edge 124*a-d* of the shelf panel 104, then the light emitted therefrom can be dispersed through the shelf panel 104 and thereby across the product(s) disposed on the shelf panel 104 by virtue of the reflective and refractive nature of the material making up the shelf panel 104. A similar phenomenon may occur if the first plurality of lights 156*a* is oriented to emit light across and/or above the upper surface 116 of the shelf panel 104, or if the first plurality of lights 156*a* is oriented to emit light across and/or below the lower surface 120 of the shelf panel 104.

The second plurality of lights 156*b* may be oriented in a second direction relative to the shelf panel 104 such that the light emitted by the second plurality of lights 156*b* is directed toward the product(s) disposed on the shelf panel 104, the shelf panel 104 itself or areas adjacent to the shelf panel 104.

The third plurality of lights 156*c*, on the other hand, may be oriented in a third direction that is different from the first direction and/or the second direction. In particular, the third direction may be away from a particular edge 124*a-d* of the shelf panel 104. For example, the third plurality of lights 156*c* can be oriented relative to the shelf panel 104 such that the third direction is between approximately 90° and approximately 270° from the upper surface 116 of the shelf panel 104. In particular, the third direction can be between approximately 135° and approximately 225° from the upper surface 116 of the shelf panel 104 and, more particularly, the third direction can be between approximately 170° and approximately 190° from the upper surface 116 of the shelf panel 104. These angles are provided as examples and may vary depending on the specific area of focus desired within the enclosure and proximity to the shelf panel 104.

Because the first, second, and third pluralities of lights 156*a-c* may be oriented to emit light in the first direction, the second direction, and the third direction, respectively, each of which can be a different direction, the first, second, and third pluralities of lights 156*a-c* may be disposed on various sides of a circuit board 180 (shown in FIG. 5). On which side each of the first, second, and third pluralities of lights 156*a-c* are disposed depends on which direction each of the pluralities of lights 156*a-c* faces. For example, as illustrated in FIG. 5, because the first and second pluralities of lights are oriented to point toward the shelf panel 104, the first and second pluralities of lights 156*a*, 156*b* can be placed on an inner surface 180*a* of the circuit board 180. So configured, the first and second pluralities of lights 156*a*, 156*b* can emit light toward the shelf panel 104 through the opening 176 in the housing 152. On the other hand, because the third plurality of lights 156*c* may be oriented to emit light in a direction that is away from the shelf panel 104, the third plurality of lights 156*c* may be disposed on an outer surface 180*b* of the circuit board 180.

The illumination module 112 may be powered by any known methods of supplying power to lights from a power supply 208, as shown in schematic form for example in FIG. 4. For example, the illumination module 112 may be configured to receive power through induction from the power supply 208. In such an example, the illumination module 112 may include any additional structure necessary to inductively receive power. Similarly, the illumination module 112 may receive power from the power supply 208 through a conductive manner. In such examples, the illumination module 112 can include any additional structure necessary to conductively receive power. In other examples, the illumination module 112 can be coupled to a power supply of a refrigerator or other appliance or cabinet in which the shelf 100 may be positioned. One such example is through the use of frictional, spring-loaded power contacts. In another such an example, the illumination module 112 can include a plurality of wires for hardwiring into the power supply of the refrigerator, which may be located near the rear of the refrigerator or other appliance or cabinet in which the shelf 100 may be positioned. Additionally, the power supply 208 may be an independent source of power coupled to illumination module 112. For example, the power supply 208 can be a battery pack or a rechargeable battery pack coupled to the shelf assembly 100. Alternatively, the power supply 208 may be individual batteries used individually instead of a battery pack.

As illustrated in FIG. 5, the lens 160 is coupled to the housing 152 such that the set of lights 156 is disposed between the lens 160 and the housing 152. As the set of lights 156 emits light, the light emitted therefrom will expand in all directions thereby illuminating everything in the direction the particular plurality of light is oriented. Often, however, it may not be desirable to emit light in such a fashion because the light may disperse too broadly thereby providing very little intensity of light in the particular direction. Advantageously, the lens 160 may be used to focus the light so that the light emitted from each plurality of lights 156a-c of the set of lights 156 is sufficiently focused in a particular direction.

Finally, as illustrated in FIGS. 1 and 2, one version of the shelf assembly 100 can include the trim component 114 that is operably coupled to the illumination module 112 and extends along a width of the first edge 124a of the shelf panel 104. Other versions may not require the trim component 114. In general, as illustrated in FIG. 5, the trim component 114 includes a face 184 and one or more securing arms 188 extending from the face 184. The face 184 includes a general round surface that extends between the one or more securing arms 188. Additionally, while not illustrated herein, the face 184 includes a plurality of transparent portions that extend along a portion of the face 184. Advantageously, the plurality of transparent portions may be used to visually depict information to an individual near the shelf assembly 100 because the plurality of transparent portions is configured to permit light emitted from the set of lights 156 to pass therethrough. In particular, the plurality of transparent portions is arranged on the face 184 such that the plurality of transparent portions create an image. For example, the image can be a logo of a brand or company that makes the product(s) disposed on the shelf panel 104, a logo of a brand or company that manufacturers the shelf assembly 100, a logo of a brand or company that has the shelf assembly 100 disposed in a storefront, a universal product code ("UPC") for the product(s) disposed on the shelf assembly 100, and/or other message conveyed to an individual within sight of the face 184.

The embodiment illustrated in FIG. 5 includes, by way of example, a first securing arm 188a and second securing arm 188b. In particular, the first securing arm 188a includes a first leg portion 192 and a first engagement portion 196 that extends from the first leg portion 192 and is configured to engage the housing 152 of the illumination module 112. The first leg portion 192 extends from an upper portion 184a of the face 188 in a direction away from the face 188 toward the shelf panel 104. The first engagement portion 196 extends from an end of the first leg portion 192 such that the engagement portion 196 releasably secures the first leg portion 192 to the first leg 164 of the housing 152. For example, the first engagement portion 196 can be a hook that couples to the first leg 164 of the housing 152 of the illumination module 112 via a friction fit, snap-fit, or any other mechanical securement mechanism.

Similarly, the second securing arm 188b includes a second leg portion 200 and a first engagement portion 204 that extends from the first leg portion 200 and is configured to engage the housing 152 of the illumination module 112. The second leg portion 200 extends from a lower portion 184b of the face 188 in a direction away from the face 188 toward the shelf panel 104. The second engagement portion 204 extends from an end of the second leg portion 200 such that the second engagement portion 204 releasably secures the second leg portion 200 to the second leg 168 of the housing 152. For example, the second engagement portion 204 can be a hook that couples to the second leg 168 of the housing 152 of the illumination module 112 via a friction fit, snap-fit, or any other mechanical securement mechanism. Accordingly, because the first leg portion 192 of the trim component 114 is releasably coupled to the first leg 164 of the housing 152 of the illumination module 112 and the second leg portion 200 of the trim component 114 is releasably coupled to the second leg 168 of the housing 152 of the illumination module 112, a length of the first leg portion 192 is greater than a length of the second leg portion 200. However, the length of the first and second leg portions 192, 200, respectively, can be different if the length of the first and second legs 164, 168 of the housing 152, respectively, is different than described above.

Further, as illustrated in FIG. 4, the shelf assembly 100 may also include a controller 212. In particular, the controller 212 may be communicatively coupled to the illumination module 112 and the power supply 208. So configured, the controller 212 may be used to selectively supply power to each plurality of lights in the illumination module 112. As will be discussed in further detail below, the illumination module 112 is configurable between a first configuration and a second configuration. In the first configuration, the controller 212 may be used to supply power to the first and third pluralities of lights 156a, 156c of the illumination module 112. In the second configuration, the controller 212 may be used to supply power to the second plurality of lights 156b of the illumination module 112. To alternate the illumination module 112 between the first and second configurations, the controller 212 may have logic instructing the controller 212 to switch from the first configuration to the second configuration, or from the second configuration to the first configuration. The controller 212 may execute the logic in response to a signal received from an external sensor. Additionally, the controller 212 may execute the logic at predetermined times throughout the day. Further, the controller 212 may be disposed within the illumination module 112. In other examples, the controller 212 can be remote from the illumination module 112 and coupled thereto wirelessly or through a wired connection.

Once the illumination module 112 is coupled to a selected edge 124a-d of the shelf panel 104 and properly powered, the illumination module 112 may operate in several different configurations. In particular, the illumination module 112 may be operable between a first configuration and a second configuration. In the first configuration, the controller may be configured to deliver power to at least the first plurality of lights 156a thereby illuminating the product(s) disposed on the shelf panel 104 and/or the shelf panel 104 itself. Additionally, in the first configuration, the controller may be configured to supply power to the third plurality of lights 156c thereby illuminating the trim component 114 so that the image disposed on the trim component 114 is visible to an individual within view of the shelf assembly 100. The third plurality of lights 156c may illuminate the trim component 114 because the third plurality of lights 156c are oriented to emit light in the direction toward the trim component 114.

It is desirable to illuminate the product(s) disposed on the shelf panel 104, adjacent to the shelf panel 104 and/or the shelf panel 104 itself when an individual is browsing the product(s). Accordingly, the illumination module 112 may be in the first configuration when a door of the enclosure is opened and/or remains in the open position. In the first configuration, the illumination module 112 may be configured to stop transmitting power to at least the first and/or third plurality of lights 156a, 156c after the door of the enclosure remains in the open position for a certain period of time. Alternatively, the illumination module 112 may be configured to continuously supply power to the first and third pluralities of lights 156a, 156c until the door of the enclosure is closed. Further, the controller may receive a signal indicative of an individual being in front of the shelf assembly 100 from, for example, a sensor disposed within the refrigerator. In response to receiving the signal, the controller may supply power to the first and third pluralities of lights 156a, 156c thereby placing the illumination module 112 in the first configuration.

Further, in the second configuration, the illumination module 112 is configured to supply power to only the second plurality of lights 156b thereby illuminating the product(s) disposed on the shelf panel 104, adjacent to the shelf panel 104 and/or the shelf panel 104 itself thereby reducing and/or eliminating germs growing or disposed on the product(s) placed on or stored adjacent to the shelf panel 104 and/or the shelf panel 104 itself. In particular, the controller may transition the illumination module 112 from the first configuration to the second configuration in response to a triggering event. The illumination module 112 may be in the second configuration when the door of the enclosure is in the closed position (e.g., the triggering event) and may immediately or contemporaneously provide power to the second plurality of lights 156b when the door is closed. Once the door is closed, the illumination module 112 may continuously supply power to only the second plurality of lights 156b until the door is again opened. However, certain components and/or materials of the enclosure, certain components and/or materials of the shelf assembly 100, and/or certain products disposed on the shelf panel 104 may not be adapted to receive light in a wavelength capable of reducing and/or eliminating germs for prolonged periods of time. The prolonged exposure can potentially damage the enclosure, shelf assembly 100, and/or products disposed on the shelf panel 104.

Accordingly, it may be desirable for the illumination module 112 to provide power to the second plurality of lights 156b intermittently thereby emitting the germicidal light for short periods of time potentially avoiding any damage or harm to the enclosure, areas of focus within the enclosure, shelf assembly, and/or products disposed on the shelf panel 104. For example, the illumination module 112 can provide power to the second plurality of lights 156b for a period of time equivalent to the amount of time that passes between the door of the enclosure opening a first time and the door of the enclosure opening a second time. In other examples, the illumination module 112 can provide power to the second plurality of lights 156b for a period of time equivalent to the amount of time necessary to reduce and/or eliminate a particular type of germ that commonly grows on the product(s) disposed on the shelf panel 104 or on focused areas adjacent to the shelf panel 104. In yet other examples, the illumination module 112 can provide power to the second plurality of lights 156b for predetermined amounts of time such as, one second, two second, three seconds, four seconds, five seconds, six seconds, seven seconds, eight seconds, nine seconds, ten seconds, greater than ten seconds, greater than fifteen seconds, greater than twenty seconds, greater than twenty five seconds, greater than thirty seconds, greater than one minute, greater than a minute and a half, greater than two minutes, greater than two and a half minutes, greater than three minutes, greater than three and a half minutes, greater than four minutes, greater than four and a half minutes, greater than five minutes, and/or greater than ten minutes.

While the above discussion assumes that the door of the enclosure is not transparent, some doors include at least a portion thereof that is transparent. In such doors, it is possible for an individual to see the product(s) disposed on the shelf panel 104 without needing to open the door. So configured, the illumination module 112 may not include a triggering event that causes the illumination module 112 to transition from the first configuration to the second configuration. Accordingly, the illumination module 112 may be configured to communicate with other devices (e.g., sensors) to indicate when an individual is in front of the door and when an individual is not in front of the door. So configured, the illumination module 112 may receive a signal from the device thereby triggering the illumination module 112 to transition from the first configuration to the second configuration and vice-a-versa.

The illumination module 112 may also be configured to transition from the first configuration to the second configuration based on the operating hours of a location in which the enclosure with the shelf assembly 100 is disposed.

The foregoing description is provided as an example of embodying the present disclosure but is not intended to be limiting of the disclosure or of any invention based thereon. Rather, the scope of any invention based on the disclosure can be defined by the following claims and also includes all equivalents thereof that fall within the spirit and scope of the claims and the disclosure as a whole.

What is claimed:

1. A shelf comprising:
   a shelf panel having an upper surface, a lower surface, and an edge that extends between the upper and lower surfaces including a front edge portion and a rear edge portion, the upper surface being capable of supporting articles thereon;
   at least one support bracket coupled to the shelf panel, the at least one support bracket configured to releasably couple the shelf panel to an enclosure adjacent to the rear edge portion thereof, such that the front edge portion faces forwardly from the enclosure when the shelf panel is coupled thereto;
   an illumination module mounted to the front edge portion, the illumination module comprising:
      a first plurality of lights emitting visible light when powered, the first plurality of lights oriented in a first direction away from the shelf panel; and
      a second plurality of lights having a germicidal effect when powered, the second plurality of lights oriented in a second direction to direct light into the shelf panel and at least one of above or below the shelf panel to apply the germicidal effect to products within the enclosure, the first and second directions being different;
   wherein the shelf panel is movable within the enclosure via the at least one support bracket to dispose the illumination module in a desired location for the germicidal effect of the second plurality of lights.

2. The shelf of claim 1, further comprising a trim component releasably coupled to the illumination module.

3. The shelf of claim 1, wherein the illumination module is selectively operable between (a) a first configuration, where the first plurality of lights receives power to visibly illuminate the shelf panel, and (b) a second configuration, where the second plurality of lights receives power to emit germicidal light.

4. The shelf of claim 1, wherein the second plurality of lights emit light having a wavelength between 100 and 470 nanometers (nm).

5. The shelf of claim 1, wherein the second plurality of lights comprise (a) lights emitting UVA light having a wavelength between 315 nm and 400 nm, (b) lights emitting UVB light having a wavelength between 280 nm and 315 nm, (c) lights emitting UVC light having a wavelength between 100 nm and 280 nm, and/or (d) blue LEDs emitting light having a wavelength between 400 nm and 470 nm.

6. The shelf of claim 3, wherein the illumination module comprises a third plurality of lights generating visible light when powered, and wherein, in the first configuration, the third plurality of lights receives power to visibly illuminate the shelf panel and/or a trim component.

7. The shelf of claim 2, wherein the trim component includes a face and at least one securing arm extending from the face, the face having at least one transparent portion such that light can pass through the at least one transparent portion.

\* \* \* \* \*